United States Patent [19]
Barry et al.

[11] Patent Number: 5,691,478
[45] Date of Patent: Nov. 25, 1997

[54] DEVICE AND METHOD FOR REMOTE ZEROING OF A BIOLOGICAL FLUID PRESSURE MEASUREMENT DEVICE

[75] Inventors: Robert L. Barry, Queensbury; Robert F. Alexander, Lake George, both of N.Y.

[73] Assignee: Schneider/Namic, Glens Falls, N.Y.

[21] Appl. No.: 478,300

[22] Filed: Jun. 7, 1995

[51] Int. Cl.$^6$ .......................... G01L 9/06; A61B 5/0215
[52] U.S. Cl. ................ 73/721; 73/717; 73/720; 73/726; 73/727; 128/675; 128/673
[58] Field of Search ...................... 128/672, 673, 128/675, 748; 73/718, 720, 721, 724, 726, 727, 715, 717, 716, 747, 748, 749, 750, 751

[56] References Cited

U.S. PATENT DOCUMENTS

| | | |
|---|---|---|
| 2,105,127 | 1/1938 | Petroe . |
| 2,600,324 | 6/1952 | Rappaport . |
| 2,615,940 | 10/1952 | Williams . |
| 3,273,447 | 9/1966 | Frank . |
| 3,590,809 | 7/1971 | London . |
| 3,590,818 | 7/1971 | Lemole . |
| 3,611,811 | 10/1971 | Lissau . |
| 3,868,679 | 2/1975 | Arneson . |
| 3,996,927 | 12/1976 | Frank . |
| 4,010,449 | 3/1977 | Faggin et al. . |
| 4,342,218 | 8/1982 | Fox .............................. 128/673 X |
| 4,431,009 | 2/1984 | Marino, Jr. et al. . |
| 4,466,290 | 8/1984 | Frick ................................ 73/756 |
| 4,557,269 | 12/1985 | Reynolds et al. . |
| 4,648,406 | 3/1987 | Miller . |
| 4,669,484 | 6/1987 | Masters . |
| 4,672,974 | 6/1987 | Lee . |
| 4,691,710 | 9/1987 | Dickens et al. ............... 128/672 X |
| 4,763,649 | 8/1988 | Merrick . |
| 4,769,001 | 9/1988 | Prince . |
| 4,779,626 | 10/1988 | Peel et al. ..................... 128/673 X |
| 4,820,265 | 4/1989 | DeSatnick et al. . |
| 4,902,277 | 2/1990 | Mathies et al. . |
| 5,098,384 | 3/1992 | Abrams ............................ 73/747 X |
| 5,103,832 | 4/1992 | Jackson . |
| 5,133,358 | 7/1992 | Gustafson et al. . |
| 5,280,789 | 1/1994 | Potts ............................. 128/672 X |

OTHER PUBLICATIONS

William Grossman, "Pressure Measurement," *Cardiac Catheterization, Angiography and Intervention* (Lea & Febiger, 4th Ed., 1991) (pp. 123–142).

R. H. S. Murray and N.A. Howe, "A Calibration System for Catheter Transducer Pressure Measurement," *Biomedical Engineering* (May 1976), p. 180.

NAMIC's Morse Perceptor Manifold with Compensation Port.

Primary Examiner—George M. Dombroske
Assistant Examiner—Joseph L. Felber
Attorney, Agent, or Firm—Kenyon & Kenyon

[57] ABSTRACT

A device and method for remotely zeroing a hydrostatic pressure compensation device are described which permit a fluid transducer, such as is used in conjunction with an intravenous catheter for the measurement of blood pressure, to be zeroed regardless of its elevation. A hydrostatic pressure compensation tube is placed in closed fluid communication with both faces of the transducer so as to provide the same pressure to each side. As an example, the transducer may measure the deflection with a piezoresistive or piezoelectric crystal or may alternatively utilize a semiconductor membrane with implanted resistive elements. The transducer may be coupled or formed integral to a manifold. In such a device, the transducer may be zeroed at any vertical position.

27 Claims, 6 Drawing Sheets

DEVICE AND METHOD FOR REMOTE ZEROING OF A BIOLOGICAL FLUID PRESSURE MEASUREMENT DEVICE

FIELD OF THE INVENTION

The present invention relates to a device and method for remote zeroing of a pressure-compensating measurement device. In particular it relates to a device and method for remotely zeroing a device that measures the pressure of biological fluids.

BACKGROUND OF THE INVENTION

In the course of monitoring biological fluid pressure using a catheter coupled to the monitoring face of a transducer that is external to the body of a patient, the maintenance of proper instrument readings free from hydrostatic pressure errors presents certain difficulties. As an example, rather than measure the blood pressure by itself, previous blood pressure monitors have had to take into account the hydrostatic pressure due to the vertical column of fluid between the point at which the blood pressure measurement is taken (typically the heart or an artery) and the transducer. If the point at which the measurement is taken is displaced vertically from the transducer (hereinafter the origin from which vertical heights are measured), as is usually the case, the vertical height difference between the two points is non-zero and hence the hydrostatic fluid pressure is non-zero. These difficulties have generally been addressed by the use of pressure-compensating measurement devices. In such a device, the monitoring face of the transducer measures the blood pressure plus the hydrostatic component, as before, but an opposite face, the so-called "compensating face," measures an amount of pressure, independently applied, equal to the aforementioned hydrostatic pressure.

The design for such a system may also be had by reference to R. H. S. Murray and N. A. Howe, "A Calibration System for Catheter Transducer Pressure Measurement," *Biomedical Engineering*, pp. 180–182 (May 1976), although it should be noted that the embodiment described therein is in the context of a back-calibration. As such, the pressure applied to the compensation face is less than atmospheric rather than greater than atmospheric. Of course, in a closed system, it is conceivable that the measured pressure may be less than atmospheric. In such a case, the compensating pressure may be closer to that used in the Murray, Howe reference.

For example, blood pressure catheters are coupled at their proximal end to a manifold and at their distal end to the patient's blood. Manifolds in current use often have an integrally formed or coupled transducer. In these designs, the pressure measured at the transducer equals the pressure of blood at the distal tip of the catheter plus a hydrostatic pressure component. This hydrostatic pressure component arises due to the height of the fluid column between the elevation of the catheter distal tip and the transducer. If the height of the fluid column, as measured vertically from the transducer, is non-zero, the hydrostatic pressure component will be non-zero because it will be due to the weight per unit area of a non-zero-height column of water. Then, if the hydrostatic pressure component is non-zero, the pressure at the transducer will not equal the blood pressure, but rather will equal the blood pressure plus this non-zero hydrostatic component. While the non-zero hydrostatic component, once measured, may be subtracted from the pressure reading on the monitor, the practitioner must still either fix the transducer at that elevation, the so-called "reference" elevation, or at least return it with precision to that predetermined reference elevation when a measurement is to be made. Otherwise, the value of the hydrostatic component would vary and attempts to subtract it would be meaningless. Despite attempts to maintain the transducer at the reference elevation, or to return it there, clinically significant errors may still arise due to fluctuations caused by, e.g., mechanical inaccuracies in the maintenance of the correct elevations.

Pressure compensators were developed to automatically account for such differences in height between the transducer and the catheter distal tip, without need for the physician to constantly maintain the transducer at the reference elevation. One type of pressure compensator uses a separate "compensation" tube to balance the pressure felt by both sides of the transducer. A tube is utilized, one end of which is placed and supported at the height of the catheter distal tip. The other end of the tube leads to the side of the transducer diaphragm not facing the blood pressure pulses. The diaphragm is then acted upon by three pressures: the blood pressure component, the hydrostatic component of the liquid column between the catheter tip and the diaphragm, and the hydrostatic component of the liquid column between the diaphragm and the end of the compensation tube kept at the same level as the catheter tip. As the two hydrostatic pressures are equal, due to their having the same level of liquid in each, they cancel out. This leaves the blood pressure pulses as the only net non-zero component in the measurement. In this configuration, the housing comprising the manifold and transducer may be moved at will without upsetting the pressure measurement. The proper use of pressure compensators effectively minimizes clinically significant errors in the measurement of pressure that arise from fluctuations in the hydrostatic component of the total measured pressure.

While pressure compensators have relieved practitioners of the inconvenience of having to fix the manifold and transducer for the duration of a procedure at a predetermined reference elevation, such devices and methods still suffer from the disadvantage that there is no easy way to calibrate them during the blood pressure measurement procedure. That is, there is no easy way to calibrate a value of zero pressure, as read by the monitor, so that it corresponds to a known value of zero hydrostatic pressure, during the procedure itself.

A known net or equalized value of zero hydrostatic pressure occurs when each side of the transducer diaphragm sees the same amount of pressure. This is because no diaphragm deflection occurs and, regardless of what the monitor reads, the user knows that there is no net pressure on the diaphragm in this situation. This is termed a "zeroing" or alternatively a "nulling," and entails placing an equal amount of pressure on each face of the diaphragm, taking a reading of the measured pressure with the monitor, and then resetting the monitor so that it reads zero under those conditions. Such nulling provides a reference point for, e.g., measuring an absolute value of blood pressure.

In present pressure compensators, there is no easy way to place an equal amount of pressure on each side of the transducer diaphragm during the blood pressure measurement. One cumbersome method to accomplish this nulling is to open each side of the diaphragm to atmosphere; however, this method obviously should be avoided during a sterile procedure. Another method that has been used in the past is to bring the transducer to the reference elevation (heart level) and then close off the tube leading to the patient's blood pressure. Not only does the patient's blood pressure then provide no component, but the hydrostatic pressure component is then identically zero. Of course, this technique does not allow the transducer to be zeroed at any elevation. That is, the transducer must be at a specific height, in the above example that of the catheter distal tip, to be properly zeroed.

It is desirable, therefore, to provide a device and method for simply and reliably zeroing a transducer where the zeroing is simple and may be performed without regard to the manifold's elevation with respect to the catheter distal tip.

SUMMARY OF THE INVENTION

The present invention provides a mechanism for remotely zeroing a transducer in a pressure-compensation system, wherein the elevation of the transducer and manifold, with respect to the catheter tip, may be changed during the procedure. That is, the transducer, usually contained within the body of the manifold, need not be placed at any particular level, such as catheter level, to be zeroed.

A pressure compensator for use in the present invention includes a manifold defining at least two cavities, each in fluid communication with a plurality of ports and at least two valves for controlling fluid flow through the ports. At least one of the ports is in fluid communication with a hydrostatic compensating pressure, this hydrostatic compensating pressure being equal to the pressure through a tube due the height of a fluid column. A transducer is coupled to the manifold and has a sensing face and a compensating face. The sensing face forms one wall of a measuring cavity and is disposed for pressure communication with the pressure to be measured. The compensating face forms one wall of a compensating cavity and is disposed for pressure communication with one or more of the ports adapted to be placed in pressure communication with a hydrostatic compensating pressure.

A device and method according to the present invention allows for the transducer to be zeroed remotely, that is, it may be zeroed at any elevation permitted by the length of the compensating column, so long as the elevation of the fluid in the compensating column is equal to the elevation of the tip of the catheter and is open to atmospheric pressure. The invention may be accomplished by creating a closed fluid path for selectively placing the first, sensing face of the transducer in pressure communication with the second, compensating face of the transducer while the sensing face of the transducer is isolated from the pressure of the fluid in the pressure monitoring vessel. That is, the measuring cavity is shunted to the compensating cavity. In this way, the sensing face and the compensating face see precisely the same pressure, ensuring that the transducer deflection is equal to zero.

Other objects, advantages, and characteristics of the present invention will become apparent in view of the description and accompanying drawings that follow.

DETAILED DESCRIPTION

Figure 1:
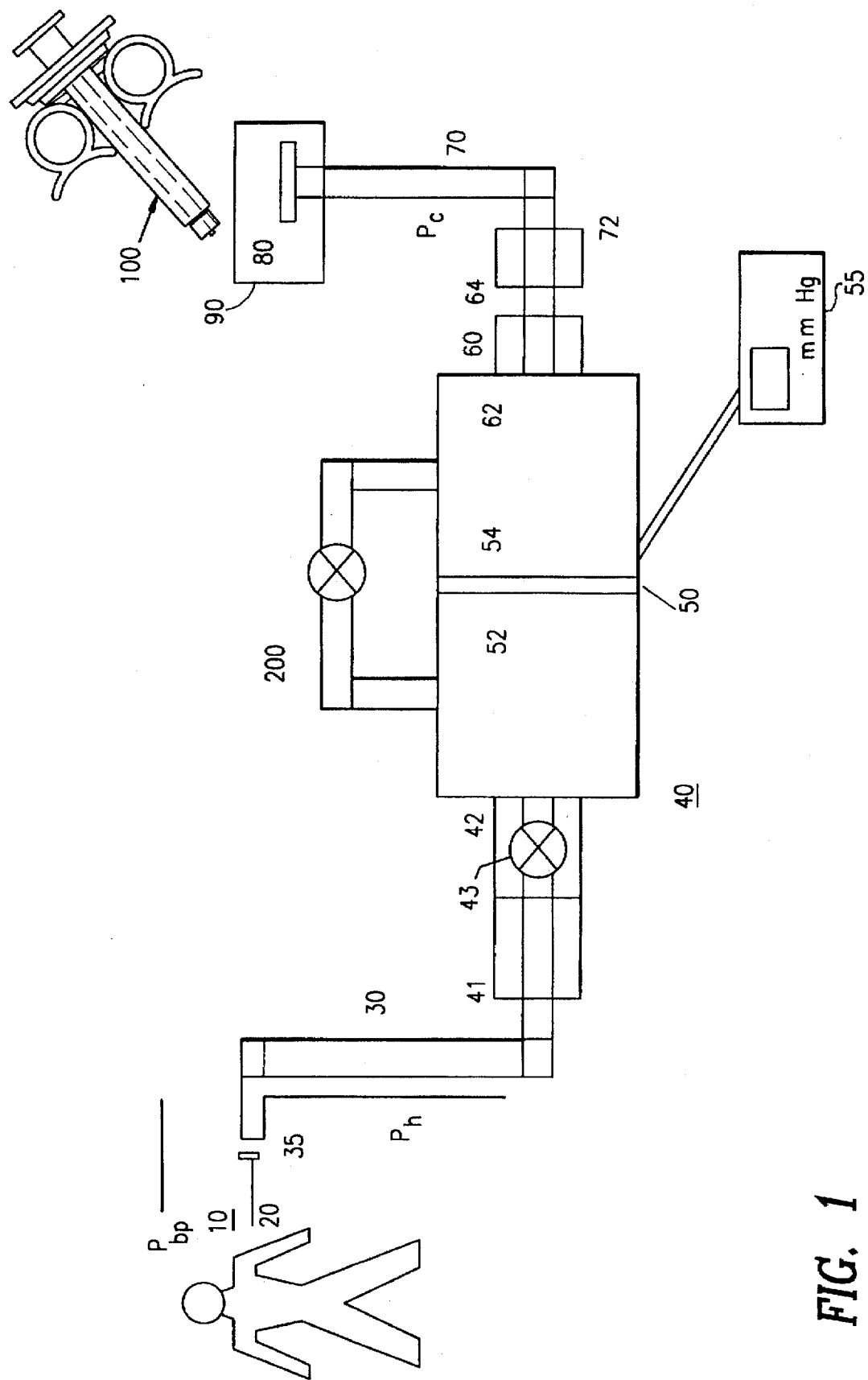
FIG. 1 illustrates a schematic view of an embodiment of a device according to the present invention.

FIG. 1 shows in schematic form a biological pressure-compensating measurement configuration with remote zeroing according to the present invention. In the measurement of pressure in biological or medical settings, a catheter 10 may be inserted into a patient to penetrate a particular site within the patient, such as the heart or a blood vessel, and to establish pressure communication between this site and a transducer 50 external to the patient. The catheter 10 has a proximal tip 35 and a distal tip 20. The distal tip 20 is inserted into a patient to establish communication with one or more biological fluids.

The proximal tip 35 of the catheter 10 is coupled in pressure communication to a pressure monitoring tube 30. The term "pressure communication" is used herein to describe a relation between a set of fluid handling tubes or vessels in which the vessels are coupled such that the pressure of the fluid in the interior of one of the vessels is transmitted to the other vessel. Pressure communication between a set of vessels may be achieved by placing them in fluid communication with one another, or if fluid communication is not desirable, separating them by a membrane capable of transmitting a pressure. It is known, for example, to establish a closed fluid communication relation between two vessels with a luer fitting. The pressure monitoring tube 30 and all fluid carrying tubes described below may be of any tubing suited for carrying biological fluids and capable of being coupled in pressure communication with other biological fluid handling tubes or vessels or with an embodiment of a transducer 50.

Pressure monitoring tube 30 is coupled in pressure communication to the transducer 50 according to known methods. The combination of the monitoring tube 30 from the patient and the transducer 50 comprise a detector for a first pressure corresponding to the sum of the blood pressure $P_{bp}$ and the hydrostatic pressure $P_h$ due to the height of the fluid column between the distal tip of the catheter 20 and a manifold 40. As shown in FIG. 1, pressure monitoring tube 30 is coupled to the transducer 50 by way of a connector 41 and a pressure monitoring port 42, one of a plurality of ports integral to a housing such as the manifold 40. A first valve means 43 may be actuated to establish or interrupt fluid and pressure communication through pressure monitoring port 42. Valve means 43 may comprise any type of valve capable of establishing or interrupting fluid and pressure communication. As shown in FIG. 1, the transducer 50 is integrated into manifold 40; in other words, the transducer 50 is permanently coupled to the manifold such that each of the sensing surfaces of the transducer 50 may be placed in pressure communication with one or more of a plurality of ports of the manifold 40. Additionally, valves such as valve 43 may be integrated into the design of the manifold 40.

The transducer 50 most preferably is planar. A requirement of a transducer 50 which is usable in the present invention is that it produce a detectable signal in response to an applied pressure or stress. Of course, to produce such a signal, certain transducers will require a power or voltage supply. Appropriate transducers may have, for example, a substrate on or in which is laid or formed resistive elements. A usable substrate may be a semiconductor such as silicon. Stress or pressure applied to the face of such a transducer would yield a signal proportional to the amount of stress or pressure applied because of the effect of the stress on the resistive elements. Furthermore, the transducer may comprise a piezoelectric or piezoresistive device; that is, it may have a crystal or chip which responds to stress by the creation of an electric polarization. Such a polarization creates a voltage in an isolated crystal. When pressure is applied to a surface of a first pressure responsive sensing face 52 of the transducer 50, the substrate and the electrically resistive elements, or alternatively the piezoelectric or piezoresistive crystal, are subjected to mechanical stress. The strain resulting from this applied mechanical stress modifies the physical characteristics of the transducer to an extent proportional, over at least some range of values, to the mechanical stress. By known means, such a modification may be converted directly into a signal from which the blood pressure may be ascertained. An appropriate transducer may be that sold in conjunction with the Perceptor Morse® Manifold System available from NAMIC USA Corp.

The transducer 50 also comprises a second pressure responsive compensating face 54. This face 54 is used to place an arbitrary second pressure, such as a pressure identical to the hydrostatic pressure $P_h$, on the transducer face 54. Such a second face 54 is advantageously opposite the first face, in which case the transducer deflection represents the difference between the first and second pressures. More particularly, in the case of the two faces 52 and 54 opposite one another on the same diaphragm, they comprise a mechanical means for measuring or determining the difference between the first pressure, felt by face 52, and the second pressure, felt by face 54. Of course, it should be noted that one skilled in the art could manufacture a transducer with separate faces in accordance with this invention. In such a case, the difference could be calculated electronically rather than mechanically. In either case, the difference signal is sent to a display means such as a monitor.

When each of the two faces 52 and 54 is subjected to the same applied pressure, the pressures exerted on the two faces balance, and the net measured pressure should therefore be zero. If it is not zero, the monitor 55 can be adjusted appropriately. More specifically, when each of the two faces of a transducer 50 is in pressure communication with a fluid column of fixed and equal magnitude, then the transducer diaphragm will feel no net deflection and should thus give a reading of zero or the monitor 55 can be adjusted to zero. Even more importantly, if the transducer 50 is vertically displaced, any hydrostatic pressure variations are identical and simultaneous at the two faces and as such continue to cancel each other out. Pressure compensation is thus effected. Because, in this embodiment, the compensation means is mechanical, and has a single operating element, it is very reliable.

As shown in FIG. 1, a calibration means is established by a first end 62 of a hydrostatic pressure compensation port 60 coupled in pressure communication to the compensating face 54 of the transducer 50. Compensating face 54 is on the opposite side of transducer 50 from the sensing face 52. Sensing face 52 is in pressure communication with pressure monitoring tube 30, and is thereby exposed to a blood pressure $P_{bp}$ and a hydrostatic pressure $P_h$. A proximal end of the pressure monitoring tube 30 is in pressure communication with the sensing face 52 of the transducer 50, and a distal tip, which may be the distal tip 20 of a catheter 10 attached to the pressure monitoring tube 30, is in pressure communication with a pressure to be measured at a first elevation. A first end 72 of a hydrostatic pressure compensation tube 70 is coupled in pressure communication to a second end 64 of the hydrostatic pressure compensation port 60. In addition to being in pressure communication at its first end 72 with the second end 64 of hydrostatic pressure compensation port 60 via the continuous column of fluid, second end 80 of pressure compensation tube 70 is open to atmosphere (above the column of fluid) at a second elevation.

In FIG. 1, the fluid, whose pressure $P_{bp}$ is to be measured, enters the manifold 40 via connector 41 and pressure monitoring port 42, which is coupled in pressure communication with the transducer 50. If valve 43 is open, the fluid enters the measuring cavity and impinges on the sensing face 52 of the transducer 50. At the sensing face 52, the pressure of the fluid is the sum of the blood pressure from the patient $P_{bp}$ and the pressure due to the height of the fluid column $P_h$. In FIG. 1, this would be the pressure felt by the left side of the transducer 50. If these were the only pressures in the system, it is difficult to extract the blood pressure from the sum, as discussed above. This is why a third pressure is used, the hydrostatic compensating pressure. This compensating pressure impinges on the right side of transducer 50, i.e., on the compensating face 54, thus effecting a mechanical subtraction of the hydrostatic compensating pressure from the pressure sum on the left-hand side of the transducer. The fluid used for hydrostatic pressure compensation enters the manifold 40 by way of pressure compensation port 60, via a first end 62 of port 60. If the hydrostatic compensating pressure is set equal to $P_h$, the mechanical subtraction yields the blood pressure $P_{bp}$ as the net non-zero component of pressure incident on the transducer. Thus, the blood pressure may be measured.

Figure 4:
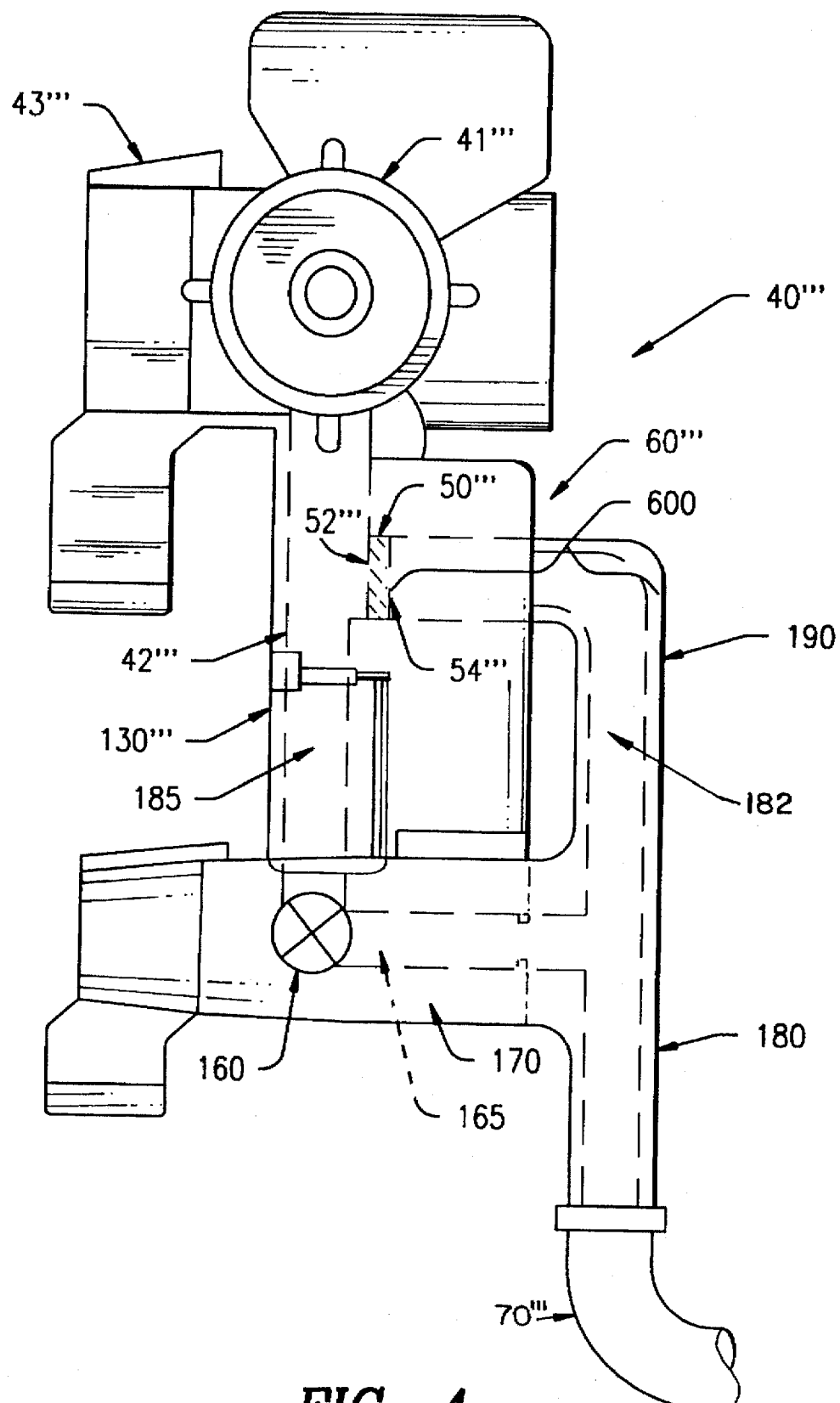
FIG. 4 illustrates an end elevational view of a third embodiment of a manifold and transducer of a pressure compensation device according to the present invention.

FIG. 4 shows an end elevational view of an embodiment of a pressure compensation device according to the present invention, to assist in the visualization of its internal structure. Essentially, it shows the transducer 50''' and related components, which are shown schematically in FIG. 1, as being located within the manifold 40'''. One can see in FIG. 4 the relation between the pressure monitoring port 42''', the transducer 50''' and the pressure compensation port 60'''. As indicated by the dotted lines, the pressure monitoring port 42''' is in pressure communication with the sensing face 52''' of transducer 50''', although pressure monitoring port 42''' may be closed off by valve 43'''. Additionally, one can see that pressure compensation port 60''', in particular by way of its first end 62''', is in pressure communication with the compensating face 54''' of transducer 50'''.

As shown in FIG. 1, the manifold may be debubbled in known fashion by, e.g., connecting a saline bag to one of the ports of the manifold, filling the manifold 40 with saline or a similar solution. The manifold 40 may then be oriented with a port pointing up so that air bubbles may escape through it. Tapping of the manifold may be necessary to dislodge bubbles.

Next, syringe 100, shown in FIG. 1, can be aspirated with, for example, a saline solution and coupled to the second end 80 of the hydrostatic pressure compensation tube 70. First end 72 of pressure compensation tube 70 is temporarily detached from the second end 64 of pressure compensation port 60. Syringe 100 is then discharged, filling the hydrostatic pressure compensation tube 70 with the fluid. Pressure compensation tube 70 is then debubbled, during which process the end 72 of the compensation tube 70 is held at a higher elevation than second end 80 to which the syringe 100 is attached.

An alternative way to debubble pressure compensation tube 70 that does not require a syringe is to attach second end 80 of the compensation tube 70 to connector 41 of the manifold 40. The compensation tube 70 is then filled with saline from the manifold 40. When compensation tube 70 is sufficiently filled, end 72 of the compensation tube is connected to second end 64 of the pressure compensation port 60. Then second end 80 of the compensation tube 70 is disconnected from the manifold and is placed in an adjustable holding device 90.

When syringe 100 is used, it remains attached to the second end 80 when the first end 72 of the hydrostatic pressure compensating tube 70 is coupled in pressure communication to the second end 64 of the hydrostatic pressure compensation port 60. Compensation port 60, in turn, is in pressure communication, which may be by way of a female luer fitting, with the compensating face 54 of transducer 50.

After syringe 100 has been discharged and pressure compensation tube 70 has been re-coupled to the manifold, syringe 100 is decoupled from the second end 80 of the hydrostatic pressure compensation tube 70, re-opening the second end 80 to atmospheric pressure. The second end 80 is then fixed to the adjustable holding device 90 capable of fixing the position of second end 80, particularly in the vertical dimension. The adjustable holding device 90 may be a pole clamp or any other known means. In this way, the second end 80 of the hydrostatic pressure compensation tube 70 may then be fixed to the adjustable holding device 90 at an elevation equal to that of the catheter distal tip 20. For example, the catheter distal tip 20 may be inserted in the patient's heart. The second end 80 of the hydrostatic pressure compensation tube 70 is then also placed at heart level, i.e., at the same elevation as the catheter distal tip 20. Second end 80 is then fixed at that elevation by the adjustable holding device 90 with second end 80 left open to atmospheric pressure. It should be noted that second end 80 may alternatively be placed higher than the level of the elevation of the patient's heart; however, in this case, the level of fluid in the compensation tube 70 must be carefully adjusted to coincide with the aforementioned heart level.

In order to take pressure-compensated measurements with a typical system, the catheter 10 is inserted into the patient and the catheter distal tip 20 is positioned at a desired point of biological fluid measurement in the patient's body, such as the heart. Pressure monitoring port 42 of the manifold 40, to which the catheter 10 is coupled in pressure communication, is initially in a closed position by way of closing valve 43. In this configuration, the sensing face 52 of the transducer 50 facing the catheter 10 is not in pressure communication with the blood pressure at distal tip 20 of catheter 10, but rather is isolated from that pressure. By opening valve 43, the sensing face 52 of the transducer 50 is placed in pressure communication with the blood pressure $P_{bp}$ seen at catheter distal tip 20 as well as the pressure $P_h$ due to the fluid in the column created by catheter 10 and pressure monitoring tube 30.

As stated previously, the pressure at the sensing face 52 of the transducer 50 during a monitoring procedure is a combination of the blood pressure $P_{bp}$ at the catheter distal tip 20 and the hydrostatic pressure $P_h$ of the column of fluid between the distal tip of the catheter 20 and the transducer 50. The pressure of the height of the fluid column in the hydrostatic pressure compensation tube 70, $P_c$, is determined by the difference between the elevation of the fluid column in the hydrostatic pressure compensation tube 70 and the elevation of the transducer 50.

If the fluid column in the pressure compensation tube 70 is fixed at the same level as the distal tip 20 of the catheter 10, then the effect of the fluid column between the catheter and the transducer is canceled by the effect of the fluid column in the compensation tube. The pressure measured by the transducer 50 is then identical to the blood pressure regardless of the level of the transducer 50.

While the use of a compensation tube allows an accurate reading of blood pressure at any transducer elevation by causing the pressure due to the effect of the fluid column between the catheter and the transducer to be canceled out, the physician cannot use this feature to zero the transducer. This is because the pressure contribution of the patient's blood cannot be easily eliminated. One must instead provide the same pressure, without blood pressure contributions, to each side of the transducer.

While compensation allows for the movement of the transducer and manifold with respect to the catheter, zeroing the transducer requires that the same pressure be placed on each face of the transducer. As a patient's blood pressure is a variable quantity, the pressure monitoring tube must be valved off via valve 43 during a zeroing procedure. But then, in order to create the same pressure on each face of the transducer, the manifold and transducer would have to be raised to heart level, i.e., the level at which second end 80 is placed. The present invention allows the transducer to be zeroed without the necessity of moving the manifold—i.e., remotely.

To remotely zero the present invention, that is, to zero the device at any elevation permitted by the length of the pressure monitoring tube 30 and the pressure compensation tube 70, the user selectively exposes, by way of a closed fluid path, both faces of the transducer simultaneously to the compensation pressure of the hydrostatic pressure compensation tube. This closed fluid path may be created by a shunt including a second valve means such as shunt valve 200. When shunt valve 200 is open, and valve 43 is closed, both faces of the transducer are exposed to the same pressure. Using such a shunt, the transducer 50 may be zeroed at any elevation by permitting both faces of the transducer 50 to be exposed to substantially identical hydrostatic pressures. Shunt valve 200 is shown as a two-way valve; however, as shown in later embodiments three-way valves may also be used.

When the shunt valve is opened, pressure in the measuring cavity will "bleed" by an actual flow of liquid. Because $P_h < P_{bp} + P_h$, a residual pressure will be present in the measuring cavity up until the time that the shunt valve is opened. The liquid in the measuring cavity will flow to the extent necessary to equalize the pressure between the measuring cavity and the compensation cavity. Of course, due to the residual pressure mentioned above, the pressure due to the height of the liquid column will be slightly greater than $P_h$ prior to the opening of the shunt valve.

Figure 2:
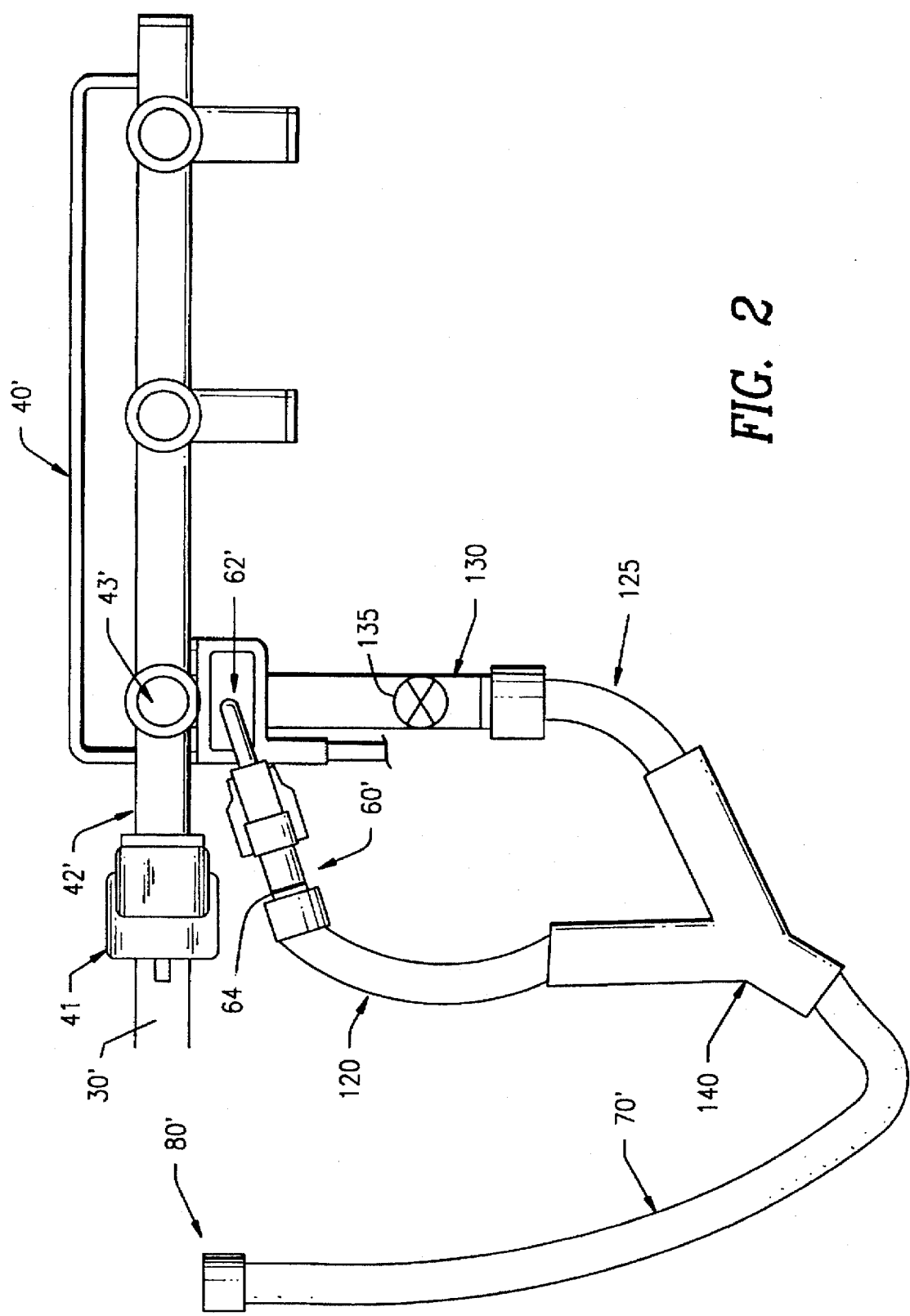
FIG. 2 illustrates a side elevational view of a first embodiment of a manifold and transducer of a pressure compensation device according to the present invention.
Figure 3:
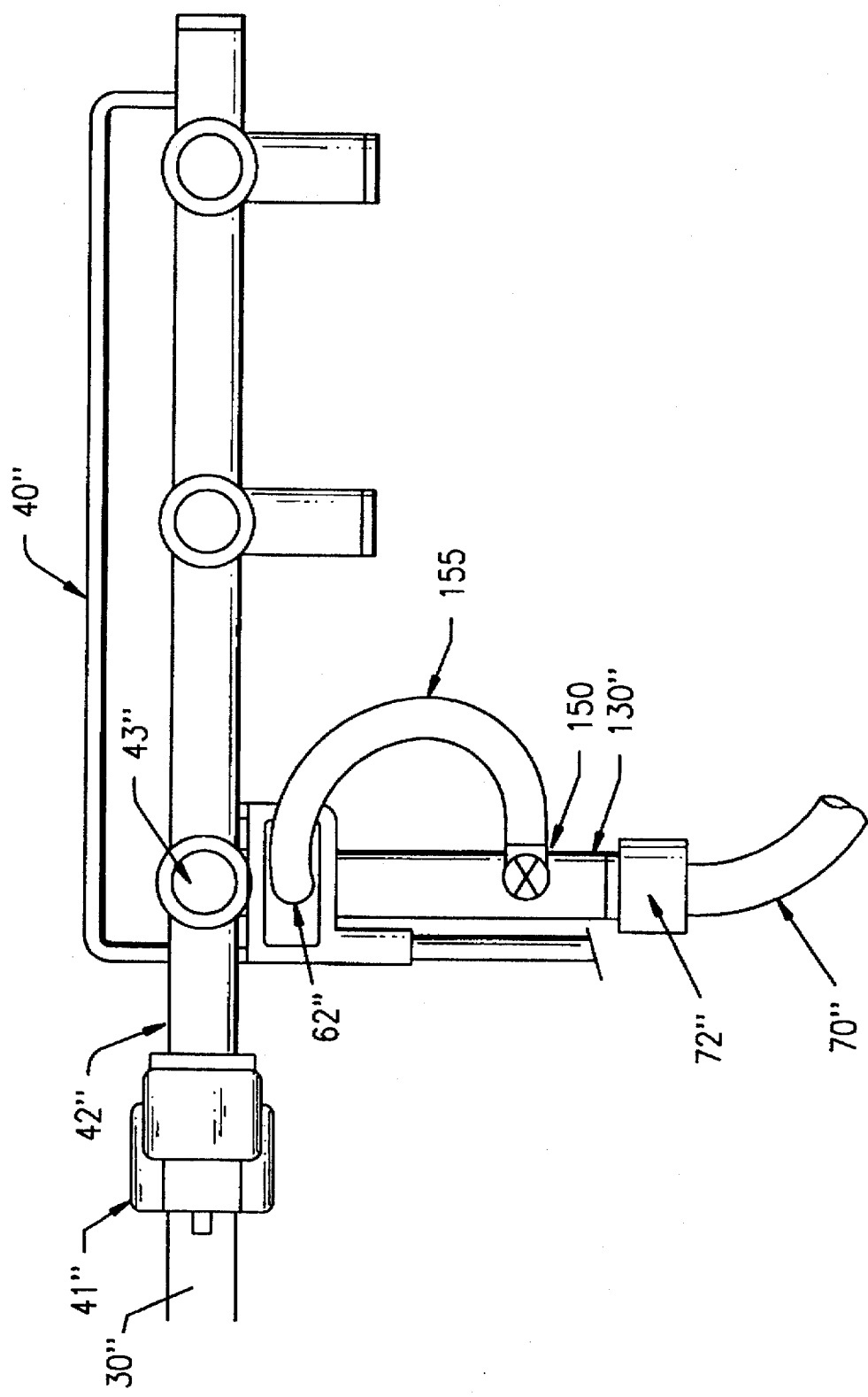
FIG. 3 illustrates a side elevational view of a second embodiment of a manifold and transducer of a pressure compensation device according to the present invention.

FIGS. 2, 3 and 4 show in greater detail the configuration of different embodiments of a device according to the present invention which include a manifold 40', 40", and 40'", respectively.

Figure 2A:
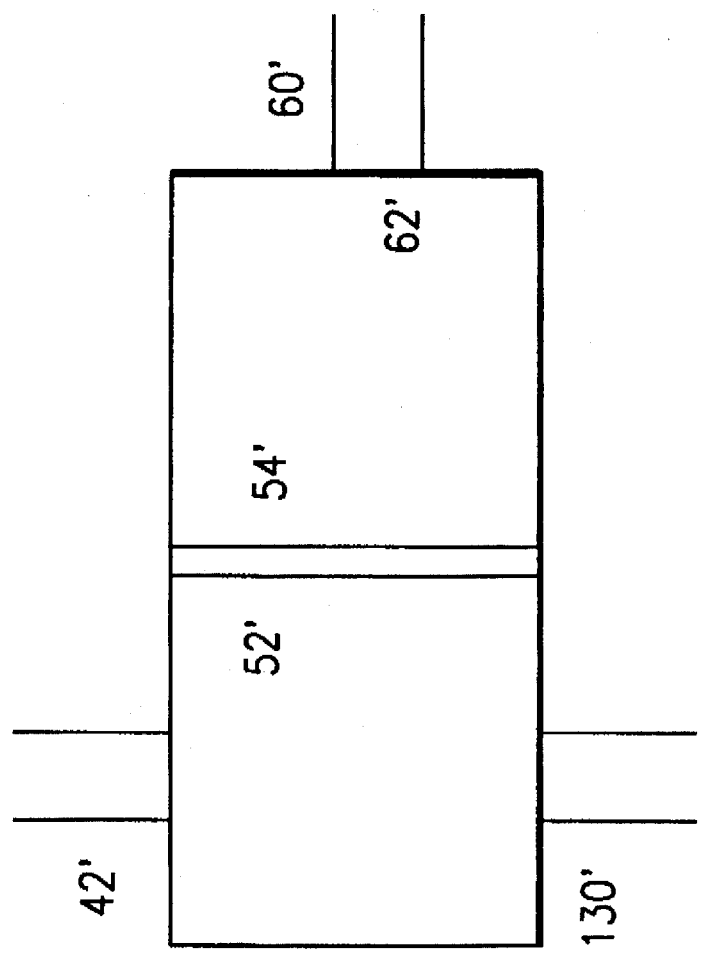
FIG. 2A illustrates a schematic view of the transducer of the pressure compensation device depicted in FIG. 2 of the present invention.

FIG. 2 shows a first embodiment of the device according to the present invention. FIG. 2A illustrates a schematic view of the transducer of the pressure compensation device depicted in FIG. 2 of the present invention. In FIG. 2, a first tube 120 is connected to second end 64' of pressure compensation port 60', and a second tube 125 is placed in pressure communication with port 130, which in turn is in pressure communication with pressure monitoring port 42', by way of a second valve means such as intervening valve 135. The free ends of the first and second tubes, 120 and 125 respectively, are then connected to two ports of a shunt means such as Y-connector 140. The third port of Y-connector 140 is connected to compensation tube 70', the second end 80' of the compensation tube 70' being, as usual, fixed at the level of the distal tip 20 (not shown) of the catheter 10 (not shown), e.g., heart level, although during zeroing the height is arbitrary. Valve 135 is a two-way valve, which, when open, exposes the sensing face 52' (as shown in FIG. 2A) of the transducer 50'(as shown in FIG. 2A) to the pressure of the fluid in pressure compensation tube 70'.

To zero the transducer via the present invention, valve 43' is closed and valve 135 is opened to expose sensing face 52' of the transducer 50' to the same pressure as seen by compensating face 54' (as shown in FIG. 2A) of transducer 50'. The output of the transducer my then be set equal to zero. It should be noted that, depending on the value of $P_{tp}$ at the time the valve is closed, the pressure in the measuring cavity may be greater or less than $P_h$. If so, i.e., if $P_h \neq P_c$, the final pressure, after the valved shunt means equalizes the pressure, may not be equal to $P_h$. In fact, the final pressure may be such that the level of the fluid column in the compensating tube 70' may be somewhat changed. While the two faces 52' and 54' of the transducer 50' may see a negligible difference in pressure due to transducer thickness and residual air in the system, this difference is invariant to elevation changes in the device, and so does not interfere with the zeroing of the transducer 50'. This is the case for all three embodiments as described herein. When the output of the transducer 50' has been set to zero, valve 135 is closed, isolating sensing face 52' from the pressure in pressure compensation tube 70'. Pressure monitoring can begin by opening valve 43' to expose sensing face 52' of transducer 50' to the pressure of the fluid in pressure monitoring tube 30'. The transducer can be re-zeroed, as described above, at any time without the necessity of returning the system to heart level. If necessary, means for bleeding the measuring cavity after zeroing may also be provided.

Figure 3A:
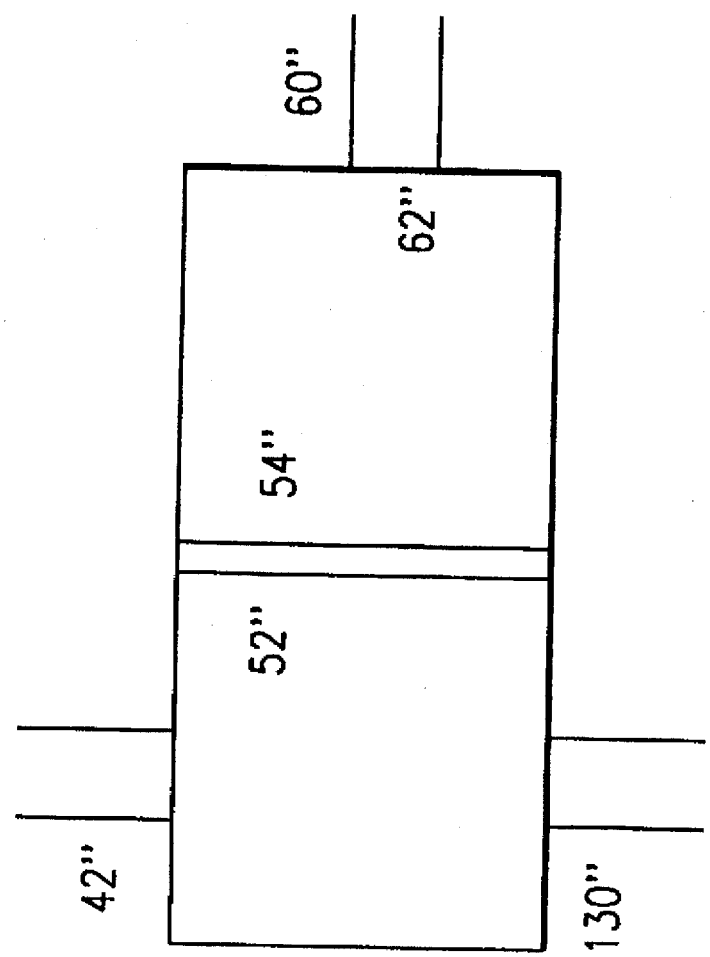
FIG. 3A illustrates a schematic view of the transducer of the pressure compensation device depicted in FIG. 3 of the present invention.

Alternative embodiments of the present invention are also possible. In a second embodiment, shown in FIG. 3 and 3A, a first port of a valved shunt means such as three-way valve 150 is connected to first end 62" of pressure compensation port 60" (as shown in FIG. 3A) by way of shunt 155. A second port of the three-way valve 150 is in pressure communication with the monitoring port 42", and the remaining port of the three-way valve 150 is coupled in pressure communication to end 72" of the pressure compensation tube 70".

To zero the transducer 50" (as shown in FIG. 3A), valve 43" is closed, isolating sensing face 52" of transducer 50" from the pressure of the fluid in pressure entering via monitoring port 42". Then valve 150 is actuated to an open position that exposes sensing face 52" and compensating face 54" (as shown in FIG. 3A) of the transducer 50" to substantially identical hydrostatic pressure, that is, the compensation pressure of the fluid in pressure compensation tube 70". Zeroing of the transducer 50" may then be done. Once the transducer reading is set equal to zero, valve 150 may be actuated to a closed position to isolate sensing face 52" of transducer 50" from the compensation pressure in pressure compensation tube 70". Valve 43" may then be opened, establishing pressure communication between sensing face 52" of transducer 50" and the pressure monitoring tube 30". As with the embodiment shown in FIG. 2 and described immediately above, the transducer 50" may be re-zeroed at any time.

An added advantage of the embodiment shown in FIG. 3 is that the pressure compensation tube can be filled from the manifold without having to connect or disconnect either end of the compensation tube from the holding device (not shown) or the compensation port.

A third embodiment of the present invention is shown in FIG. 4. This embodiment is similar to the embodiment illustrated in FIG. 3, but in this case a shell having an interior channel is used. In FIG. 4, such a shell has the shape of a reverse "F" shape. Of course, as viewed from the opposite side, such a shell has the shape of a normal "F". In the following description, the upper rung of the "F" is denoted element 600, the lower rung is denoted element 170, the section between the compensation tube 70'" and the lower rung is denoted 180, and the section between the two rungs is denoted 190. Each of these sections has an associated channel in its interior.

In this third embodiment, the valved shunt means includes a two-way valve 160 which is connected between port 130'" at channel 185 and lower rung 170 at channel 165. Port 130'" provides pressure communication, via channel 185, between channel 165 and the sensing face 52'" of the transducer 50'". Channel 165 is generally in the interior of lower rung 170, which, as can be seen in FIG. 4, is in pressure communication with compensation port 60'". The upper rung 600 has a first opening in pressure communication with compensation port 60'". Section 190 provides pressure communication between the upper rung 600 and the lower rung 170, as well as pressure communication to a third opening in closed fluid communication with compensation tube 70'" through section 180.

For remote zeroing, valve 43'" is closed and valve 160 is opened to permit ports 60'" and 130'" to come into pressure communication with each other such that sensing face 52'" and compensating face 54'" of transducer 50'" are exposed to the same pressure and can be zeroed. After the transducer 50'" has been zeroed, valve 160 is closed to isolate sensing face 52'" from the compensation pressure. Valve 43'" can then be reopened to expose sensing face 52'" to the pressure in the pressure monitoring tube (not shown). As with the first and second embodiments, the transducer 50'" may be re-zeroed at any time by shunting the measuring and compensating cavities as described above.

Those skilled in the art will recognize that the present invention is not limited to the embodiments here described. For example, the particular choice of fluid carrying vessels used for permitting pressure communication between elements of the invention, or the choice of valve used for interrupting or establishing that pressure communication may employ any suitable known means.

What is claimed is:

1. A device for measuring pressure, comprising:
 a housing having a plurality of ports and a transducer including a sensing face and a compensating face;
 the transducer being disposed in the housing and with respect to the ports so that the sensing face independently may be put in pressure communication with a pressure to be measured and the compensating face independently may be put in pressure communication with a compensating pressure;
 a first valve means for selectively interrupting pressure communication between the sensing face and pressure to be measured; and
 a shunt means for establishing pressure communication between the sensing face and the compensating face including a second valve means for selectively interrupting pressure communication between the sensing and compensating faces.

2. A device for measuring pressure providing hydrostatic pressure compensation and remote zeroing, comprising:
   a) a housing including a measuring cavity and a compensation cavity separated by at least a transducer having a sensing face and a compensating face;
   b) a hydrostatic pressure compensation tube adapted to contain fluid and having a first end in pressure communication with the compensating cavity and a second end in pressure communication with atmospheric pressure;
   c) a pressure monitoring tube adapted to contain a fluid and having a proximal end in pressure communication with the measuring cavity and a distal tip exposed to a pressure to be measured at a first elevation;
   d) first valve means in fluid communication with the proximal end of the pressure monitoring tube and with the measuring cavity, for selectively establishing and interrupting pressure communication between the pressure monitoring tube and the sensing face of the transducer;
   e) an adjustable holding device for fixing the second end of the hydrostatic pressure compensation tube at a second elevation;
   f) a closed fluid path for placing the sensing face of the transducer in pressure communication with the compensating face of the transducer; and
   g) valved shunt means disposed in the closed fluid path for selectively establishing and interrupting pressure communication between the sensing face of the transducer and the compensating face of the transducer;

whereby the pressure measurement device may be remotely zeroed by interrupting with the first valve means the pressure communication between the pressure monitoring tube and the sensing face of the transducer and establishing with the valved shunt means pressure communication between the sensing face and the compensating face of the transducer.

3. The device of claim 2, wherein the closed fluid path for placing the sensing face of the transducer in pressure communication with the compensating face of the transducer comprises a Y-connector.

4. The device of claim 2, wherein the closed fluid path for placing the sensing face of the transducer in pressure communication with the compensating face of the transducer comprises a two-way valve.

5. The device of claim 2, wherein the closed fluid path for placing the sensing face of the transducer in pressure communication with the compensating face of the transducer comprises a three-way valve.

6. The device of claim 2, wherein the closed fluid path for placing the sensing face of the transducer in pressure communication with the compensating face of the transducer comprises a shell having an interior channel and three ports each connected to the channel.

7. The device of claim 2, wherein the first elevation is substantially the same as the second elevation.

8. The device of claim 7, wherein the first and second elevations are substantially the same as the elevation of the distal tip.

9. The device of claim 2, wherein the pressure measured is blood pressure.

10. The device of claim 2, further comprising a catheter with a catheter distal tip in pressure communication with the pressure to be measured and a catheter proximal tip in pressure communication with the pressure monitoring tube.

11. The device of claim 10, wherein the catheter is inserted in a blood vessel.

12. The device of claim 10, wherein the catheter is inserted in a heart.

13. A device for measuring pressure with hydrostatic pressure compensation and remote zeroing, comprising:
   a) a transducer having a sensing face and a compensating face;
   b) a hydrostatic pressure compensation tube adapted to contain a fluid and having a first end in pressure communication with the compensating face of the transducer and a second end in pressure communication with atmospheric pressure;
   c) a pressure monitoring tube adapted to contain a fluid and having a proximal end in pressure communication with the sensing face of the transducer and a distal end exposed to a pressure to be measured at an elevation;
   d) first valve means for selectively establishing and interrupting pressure communication between the pressure monitoring tube and the sensing face of the transducer;
   e) an adjustable holding device for fixing the second end of the hydrostatic pressure compensation tube at an elevation substantially the same as the elevation of the distal end of the pressure monitoring tube; and
   f) shunt means including a valve means for selectively establishing pressure communication between the sensing face and the compensating face.

14. A device for measuring pressure with hydrostatic pressure compensation and remote zeroing, comprising:
   a) a manifold comprising an interior portion and a plurality of ports, the interior portion and the ports selectively in fluid communication with each other;
   b) a transducer coupled to the interior portion of the manifold and having a sensing face and a compensating face;
   c) a hydrostatic pressure compensation tube adapted to contain fluid and having a first end in pressure communication with the compensating face of the transducer and a second end in pressure communication with atmospheric pressure;
   d) a pressure monitoring tube adapted to contain a fluid and having a proximal end in pressure communication with the sensing face of the transducer and a distal tip exposed to a pressure to be measured at an elevation;
   e) first valve means for selectively establishing and interrupting pressure communication between the pressure monitoring tube and the sensing face of the transducer;
   f) an adjustable holding device for fixing the second end of the hydrostatic pressure compensation tube at an elevation substantially the same as the elevation of the distal tip of the pressure monitoring tube; and
   g) shunt means including a valve means for selectively establishing pressure communication between the sensing face and the compensating face of the transducer.

15. A method for remotely zeroing a device for measuring fluid pressure with hydrostatic pressure compensation, the device including a transducer for generating an output signal from which a measured pressure value is derived and having a sensing face and a compensating face, the device further including a first valve means for establishing and interrupting pressure communication between the fluid pressure to be measured and the sensing face of the transducer, and a zeroing means for placing the compensating face of the transducer in pressure communication with a pressure substantially equal to a hydrostatic component of a pressure communicated to the sensing face of the transducer, the device further including a closed fluid path between the sensing face and the compensating face of the transducer, the closed fluid path including shunt means including a second valve means for establishing and interrupting pressure communication between the sensing face and the compensating face of the transducer, the method comprising the steps of:

a) actuating the first valve means to interrupt pressure communication between the sensing face of the transducer and the fluid pressure to be measured;

b) actuating the second valve means to establish pressure communication between the sensing face and the compensating face of the transducer;

c) setting the measured pressure value to zero; and d) actuating the second valve means to interrupt pressure communication between the sensing face and the compensating face of the transducer.

16. An improved device for measuring internal body fluid pressure, comprising:

a housing including a transducer having first and second pressure responsive surfaces for generating a signal corresponding to fluid pressure on each face disposed therein;

a detector means for establishing fluid pressure communication between a body fluid and the first pressure responsive surface and for producing a signal corresponding to a first pressure representing the sum of the body fluid pressure plus a hydrostatic pressure component;

a calibration means for establishing a second fluid pressure on the second pressure responsive surface corresponding to the hydrostatic pressure component;

a zeroing means for establishing fluid pressure communication between the first and second pressure responsive surfaces;

a means for determining a difference between the first pressure and the second pressure; and a means for displaying the difference calculated.

17. The device of claim 16, wherein the first and second pressure responsive surfaces are opposite sides of a diaphragm.

18. The device of claim 17, wherein the diaphragm includes a piezoresistive element.

19. The device of claim 17, wherein the diaphragm includes a piezoelectric element.

20. The device of claim 17, wherein the diaphragm includes:

a substrate; and a plurality of resistive elements coupled to said substrate.

21. The device of claim 20, wherein said substrate is a semiconductor.

22. The device of claim 21, wherein said semiconductor is partially comprised of silicon.

23. The device of claim 16, wherein the hydrostatic pressure component is the pressure due to the height of the fluid column between the transducer and the point at which the body fluid pressure is sensed.

24. The device of claim 16, wherein the difference determination means is mechanical.

25. The device of claim 16, wherein the difference determination means is electronic.

26. The device of claim 16, wherein the difference display means is a monitor.

27. The device of claim 16, wherein the detector means includes a catheter with a distal tip.

* * * * *